United States Patent [19]

Kettman et al.

[11] Patent Number: 4,514,498

[45] Date of Patent: Apr. 30, 1985

[54] HYBRID CELL LINES PRODUCING MONOCLONAL ANTIBODIES DIRECTED AGAINST TREPONEMA

[75] Inventors: John R. Kettman, Carrollton; Michael V. Norgard, Plano, both of Tex.

[73] Assignee: The Board of Regents, The University of Texas System, Austin, Tex.

[21] Appl. No.: 381,929

[22] Filed: May 26, 1982

[51] Int. Cl.$^3$ .................. C12N 5/00; C12N 15/00; C07G 7/00

[52] U.S. Cl. ..................... 435/240; 260/112 R; 424/85; 424/87; 435/172.2; 935/103; 935/104; 935/105

[58] Field of Search ............... 424/85, 86, 87; 435/172, 240, 241, 948, 172.2; 436/548; 260/112 R, 112 B

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 424/85 |
| 4,271,145 | 6/1981 | Wands et al. | 424/85 |

OTHER PUBLICATIONS

Kennett et al., "Hybrid Plasmacytoma Production: Fusions with Adult Spleen Cells, Monoclonal Spleen Fragments, Neonatal Spleen Cells and Human Spleen Cells", *Lymphocyte Hybridomas*, ed. by Melchers et al., *Current Topics in Microbiology and Immunology*, Springer-Verlag, Berlin, 1978, pp. 77-91.

*Microbiology*, Pelczar, Jr. et al., McGraw-Hill, New York, 1972, pp. 624-625.

Glass, David, "Medicine's Micro Missiles", *Science Digest*, 30-31:114, (Jan. 1982).

Miller, J. N., "Value and Limitations of Nontreponemal and Treponemal Tests in the Laboratory Diagnosis of Syphilis", *Clinical Obstetrics and Gynecology*, 18:191-203 (1975).

*Primary Examiner*—Blondel Hazel
*Attorney, Agent, or Firm*—Arnold, White & Durkee

[57] ABSTRACT

Continuous hybrid cell lines for producing monoclonal antibodies directed against antigens of *Treponema pallidum* have been developed. The hybrid cell lines were established by fusing differentiated lymphoid cells primed with antigens of *Treponema pallidum* with hybridoma cells. The resulting fused cells were cloned, isolated, cultured and characterized as to antibody specificity against antigenic determinants of *Treponema pallidum*.

9 Claims, No Drawings

HYBRID CELL LINES PRODUCING MONOCLONAL ANTIBODIES DIRECTED AGAINST TREPONEMA

The Government has rights in the invention pursuant to National Institutes of Health Grant Nos. AI-16692, AI-11851 and CA-23115 awarded by the Department of Health and Human Services.

BACKGROUND OF THE INVENTION

The present invention relates to the production of monoclonal antibodies; and, in particular, to hybrid cell lines capable of continuously producing monoclonal antibodies directed against Treponema bacterial pathogens.

In recent years, the capability to produce monoclonal antibodies specific for the immunogenic determinants of bacterial cells and toxins has provided a new vista of diagnostic and immunotherapeutic agents.

The bacterial genus Treponema is associated with a variety of pathogenic diseases. Of particular significance, *Treponema pallidum* is a sexually transmitted bacterial pathogen of man responsibe for syphilis. Very little is known about *T. pallidum*, despite decades of strenuous efforts to understand this organism. The gross lack of information stems primarily from the fact that *T. pallidum* is one of the very few bacterial pathogens for man that cannot be grown in vitro like other human pathogens. Consequently, researchers attempting to elucidate the nature of the organism and the disease it produces have been confined to cultivating *T. pallidum* in the testicles of laboratory rabbits.

Untreated syphilis in man is a severe, chronic, and very complex disease that can often be extremely difficult to diagnose. Limitations with current diagnostic tools and the absence of a vaccine have allowed syphilis to flourish at the estimated frequency of approximately 350,000 cases per year in the United States alone, even with the availability of effective penicillin treatment.

Moreover, there are other treponemal diseases which perhaps have a more worldwide impact with respect to morbidity and mortality. Briefly, the treponemes that cause yaws, pinta, and bejel are treponemes morphologically and serologically indistinguishable from *T. pallidum*. These diseases are very serious worldwide, especially in the socalled third world countries. These diseases are believed to be transmitted through normal person-to-person contact, as opposed to *T. pallidum*, which is a sexually transmitted agent. As a result these particular diseases are highly contagious and devastating to large populations thereby eluding effective control.

Many attempts at vaccine development over past decades using whole cells, extracts, or adjuvant preparations of *T. pallidum* or other non-pathogenic treponemes have failed. One study reported the successful vaccination of rabbits with *T. pallidum* (Nichols) attenuated by $\gamma$-irradiation. There are several major drawbacks to this approach as a potential immunization scheme for humans. These include the impracticality of preparing massive amounts of freshly isolated and freshly irradiated treponemes, as well as the dangers associated with hypersensitivity reactions by the recipient to contaminating rabbit proteins present in treponemal suspensions.

Syphilis and other related pathogenic treponemal disease research continues to lag far behind other areas of bacterial infectious disease. In particular, the complexity of the humoral response to *T. pallidum* infection and the inability to obtain large amounts of *T. pallidum* cells for subsequent fractionation of constituent antigens have severely hampered identification of the specific immunogens of *T. pallidum* that are responsible for eliciting protective immunity in rabbits and man. The specific *T. pallidum* immunogens that remain unidentified and uncharacterized may hold the key to immunological approaches for the control of syphilis.

The somatic cell fusion of plasmacytoma cell lines with treponemal-sensitized spleen or lymph node cells to produce monoclonal antibodies specific for a treponemal species determinant provides a new and innovative way to circumvent major obstacles of the past. Once successfully carried out, a virtually limitless supply of monospecific antibodies for *Treponema pallidum* antigens will be readily available at all times. These monospecific antibodies could then be used to analyze the antigenic components of the Treponema immunogens. The isolation and characterization of specific Treponema immunogens through the use of the new hybridoma cell fusion technology may provide the materials and insights needed to understand the pathogenesis and immunological control of syphilis, yaws, pinta, and bejel through vaccine development.

The invention seeks to develop continuous hybrid cell lines which produce monoclonal antibody directed against treponemal antigens. Selected cell lines are capable of continuously producing a set of monospecific antibodies that are identical with respect to combining site specificity to a single antigenic determinant exhibited by a treponemal bacteria.

SUMMARY OF THE INVENTION

In accordance with the present invention, continuous hybridoma cell lines are established which elaborate and secrete higly specific and homogenous monoclonal antibodies to treponemal antigens, in particular *Treponema pallidum*.

In its broadest aspect, the invention involves first immunizing an animal to Treponema bacteria to develop lymphocytes and their differentiated progeny which produce antibodies directed against a priming antigenic determinant. The lymphocytes are recovered and fused with myeloma, plasmacytoma, or hybridoma cells to form somatic cell hybrids. The cell hybrids are cultured, selected, isolated and propagated in tissue culture. Thereafter, the hybrid cell lines are capable of indefinitely producing monoclonal antibodies to the selected immunizing antigens.

In accordance with the present invention there are provided continuous hybrid cell lines that produce monoclonal antibody against antigenic determinats of Treponema. Continuous cell lines have been isolated which produce monoclonal antibody directed specifically against *T. pallidum* antigens or against treponemal group antigens (antibody which cross react among several of the Treponema species). Moreover, there are provided complement fixing monoclonal antibodies which are capable of immobilizing virulent treponemes.

DETAILED DESCRIPTION OF PREFERRED EMBODIMENTS

The following discussion is in terms of the preferred embodiments of this invention, which represent the best mode known to the Applicants at the time of this application.

In accordance with the processes of this invention, test animals are stimulated in vivo for antibody production by immunization with a preparation containing Treponema bacteria. Applicants have directed their preferred embodiment to immunizing mice with a *T. pallidum* inoculum extracted from rabbit testicles.

Alternatively, normal and immune differentiated lymphocytes capable of producing antibody can be isolated from test animals, cultured, and primed with Treponema in vitro to generate cells appropriate for producing lymphocyte hybridomas. For example, such methods of in vitro stimulation with mitogens and/or antigens have been described by Robertson et al, *Microbiology* 1980 pp. 181-185 (1980) and Kettman et al, *J. Immunol. Methods* 39:203-222 (1980) or the method splenic fragment culture as described by Press et al, *Eur. J. Immunol.* 4:155-159 (1974).

The route and schedule of immunizing the host animal or cultured antibody producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of human hybrid cell lines.

After immunization, immune lymphoid cells are fused with myeloma, plasmacytoma, or hybridoma cells (hereinafter referred to collectively as myeloma cells) to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. Applicants prefer to employ immune spleen cells, since they offer a more concentrated and convenient source of antibody producing cells with respect to the mouse system.

The myeloma cells provide the basis for continuous propagation of the fused hybrid. Myeloma cells are tumor cells derived from plasma cells which show preference for bone marrow. Plasmacytoma cells are neoplastic cells derived from plasma cells. In particular, Applicants prefer to use lymphocyte hybridoma cells which secrete no immunoglobulin. Lymphocyte hybridoma cells are cells generated by the fusion of myeloma or plasmacytoma cells with normal differentiated lymphoid cells. Myeloma, plasmacytoma, and hybridomas can be selected to be devoid of immunoglobulin synthesis.

The particular species of animal from which the myeloma and immunized antibody producing cells are derived are not critical, in that it is possible to fuse cells of one species with another. However, it is preferred that the source of immunized antibody producing cells and myeloma be from the same species.

Generally the fusion techniques employed are according to the procedures set out by Kohler et al, *Eur. J. Immunol.* 6:11-19 (1976) and Kennett et al, *Lymphocyte Hybridomas—Current Topics in Microbiology and Immunology* 81: 77-91 (1978) Springer-Verlag, New York. Fusion is generally accomplished by adding a suspension of antibody producing cells to the myeloma cells in growth medium and thereafter centrifuging to form a pellet.

The fused hybrids are next screened for antibody production specific for treponemal antigens. A hybridoma which secretes antibody specific for a treponemal antigenic determinant is selected and cultured to establish a continuous cell line with stable genetic coding. The cell line can be stored and preserved in any of a number of conventional ways, including freezing and storage under liquid nitrogen. A frozen cell line can be revived and cultured indefinitely with resumed synthesis and secretion of monoclonal antibodies specific for the selected antigenic determinant. The secreted antibody is recovered from tissue culture supernatant by conventional precipitation, ion exchange, affinity chromatography, or the like. The recovered antibody can be freeze dried and stored under refrigeration for at least several weeks without significant loss of activity.

The following examples are offered to illustrate a particular embodiment of the invention but they are not intended to limit it.

A. Preparation of Antigens

*T. pallidum* (Nichols) was used for sensitizing mice and as a source of antigen in the radioimmunoassay (RIA). The organisms were cultivated in the testicles of New Zealand White rabbits, previously examined upon receipt for the absence of clinical and serological (VDRL non-reactive) evidence of *Treponema paraluis-cuniculi* infection; the animals were subsequently housed individually at 18°-20° C. with antibiotic-free food and water given ad libitum. Approximately 12 days following each intratesticular injection of $2 \times 10^7$ *T. pallidum* in one ml of serum-saline extraction medium [0.01M sodium phosphate buffer, pH 7.2, 0.85% (wt/vol) NaCl, 50% (vol/vol) heat-inactivated (56° C., 30 min) normal rabbit serum] per testicle, treponemes were extracted aerobically from minced testicles by rotary shaking at 180 rpm (23° C.) for 30 min using 10 ml of extraction medium per testicle. Gross rabbit testicular tissue debris was removed from the treponemal suspension by centrifugation twice at $500 \times g$ for 10 min at 23° C. in a 50 ml conical polypropylene centrifuge tube. Treponemes in suspension were then examined for motility, concentrated by centrifugation at $16,000 \times g$ for 20 min, suspended in phosphate buffered saline (PBS) (0.01M sodium phosphate buffer, 0.85% NaCl, pH 7.2), and enumerated by darkfield microscopy. "Fresh" treponemes were used immediately upon isolation to prepare RIA plates, which could be stored at $-70°$ C. "Aged" treponemes were produced by storing suspensions of *T. pallidum* in PBS at 4° C. for 7 days before binding to microtiter plate wells for RIA.

*T. phagedenis* biotype Reiter (Reiter treponeme) was used in a RIA to identify antibodies directed against Treponema group antigens. The organisms were maintained at 23° C. and transferred monthly in BBL Thioglycollate Medium 135C (without indicator) containing 10% (vol/vol) heat-inactivated (56° C., 30 min.) sterile bovine serum. Cells for use in RIA were cultivated for 5 days at 35° C. in large screw capped tubes containing 40 ml of BBL Spirolate Broth supplemented with 4 ml of sterile bovine serum (total vol. of 44 ml per tube). Cells from 5 tubes were collected by centrifugation, washed twice by centrifugation in 40 ml of sterile PBS, and suspended in PBS at a cell density of approximately $1 \times 10^8$ cells per ml as determined by darkfield microscopy.

A rabbit testicular antigen extract for RIA was prepared from the testicles of normal, uninfected, VDRL non-reactive rabbits for the detection of monoclonal antibodies that cross-reacted with rabbit antigens or were directed against contaminating rabbit host antigens present in *T. pallidum* suspensions (used for the sensitization of mice). Testicles were minced and extracted in serum-saline medium as described for *T. pallidum,* but centrifuged only once for 7 min at 250×g, yielding a turbid supernatant. Ten microliters of this rabbit antigen preparation were used per microtiter plate well in the RIA. Protein assays indicated that 10 microliters of this preparation contained about 120 μg of total rabbit protein and that 50% of this total protein was due to the normal rabbit serum in the serum-saline extraction medium. Preparations stored for up to 6 months at −20° C. appeared to react equally as well as freshly-prepared extracts in the RIA.

Sonicated suspensions of *T. pallidum* or *T. phagedenis* biotype Reiter were also used as RIA antigen to detect antibodies directed against either "masked", subsurface or cytoplasmic treponemal antigens. Treponemal suspensions of approximately $1\times10^8$ cells per ml in PBS were sonicated for a total of 3 min (6 min at 50% pulse) (on ice) using a stepped microtip and a Branson Sonifier Model W350 set for an output of 4 (about 40 W). Ten μl of these sonicate suspensions were used per microtiter plate well in the RIA. Unused suspension were stored at −20° C.

B. Plasmacytoma Cell Line

The mouse plasmacytoma cell line SP2/0-Ag14 (SP2/0), which is a hybrid cell line derived from SP2/HGLK formed from the hybridization between a BALB/c mouse spleen cell and the myeloma cell line X63/Ag8 described by Schulman et al, *Nature* 276: 269–270 (1978) was the cell line used in this study. SP2/0 synthesizes no Ig heavy or light chains, is resistant to 20 μg of 8-azaguanine per ml, and is killed in hypoxanthine-aminopterin-thymidine (HAT) medium. SP2/0 cells are maintained in vitro in Dulbecco's Modified Eagle's Medium with high glucose (DMEM) (Grand Island Biological Company, Grand Island, N.Y.) supplemented with 15% (vol/vol) fetal calf serum (Hy-Clone FCS; Sterile Systems, Logan, Utah), 2 mM glutamine, and 50 units of penicillin/streptomycin (GIBCO) per ml.

C. Immunization Schedule for Hybridoma Production

Adult female BALB/c mice (6–8 weeks old) were purchased from Jackson Laboratories (Bar Harbor, Me.) and used as a source of splenic lymphocytes producing antibodies against *T. pallidum* antigens. Mice were initially immunized with freshly-prepared *T. pallidum* cells in PBS ($2\times10^8$ cells/0.15 ml PBS) in complete Freunds adjuvant (1:1) intraperitoneally (IP). Three additional injections of $2\times10^7$ freshly isolated organisms (0.3 ml PBS; IP) were given on days 21, 42, and 63, and a final injection of $1.2\times10^7$ organisms in 0.4 ml PBS (0.2 ml IP and 0.2 ml intravenously) on day 84. Three days following the last injection, spleens were removed aseptically from two mice and the spleen cells were prepared for hybridoma cell fusion by gently teasing them with forceps to prepare a single cell suspension in DMEM. The cells were then washed three times with DMEM by centrifugation at 270×g for 10 min at 8° C.

D. Construction of Hybridomas

Hybridomas were produced by fusing spleen cells from the immunized mice with murine SP2/0-Ag14 hybridoma cells (SP2/0 hereinafter) using a modification of the basic procedure of Kennett et al, *Lymphocyte Hybridomas—Current Topics in Microbiology and Immunology,* Vol. 81, pp. 77–91 (1978) Springer-Verlag, New York. Suitable cell lines were obtained from Roger Kennett, University of Pennsylvania Medical School as originally set forth by Schulman et al, supra.

Plasmacytoma cells were harvested from culture in the logarithmic phase of growth, pelleted by centrifugation at 270×g for 10 min, and washed three times in DMEM. Approximately $1\times10^7$ SP2/0 cells and the washed spleen cells were mixed together at a ratio of 7 viable spleen cells per viable SP2/0 cell and pelleted by centrifugation. After the supernatant was removed, 0.2 ml of warm (37° C.) polyethylene glycol (35% wt/vol in DMEM; PEG 1000; J. T. Baker Chemical Company, Phillipsburg, N.J.) was added to the pellet to cause cell fusion.

The cells were then pelleted, washed in DMEM, and resuspended in 25–60 ml of DME-Hy medium (see Kennett et al, supra at p. 78) at approximately $4\times10^6$ cells/ml and plated under the conditions of limiting dilution in 50 μl aliquots in 96 well microtiter plates (Costar Plastics, Vineland, N.J.). This fusion prooedure differs from the method of Kennett et al, supra in that the SP2/0-spleen cell mixture, PEG, and DMEM are all kept at 37° C. for the fusion processes. The cell pellet is loosened with a glass rod to ensure gentle mixing of the cells and the cells remain in PEG for 3 min. at 37° C. and for approximately 5 min. at 8° C. (during centrifugation).

A two-fold concentration of HAT selection components in media, as specified in Littlefield et al, *Science* 145: 709–710 (1964), was added to each well (50 μl) on day 2, followed by a 100 μl of HAT-medium on day 4. Hybrids could be observed after 6–10 days. Wells which contained growing cells were subdivided into another 96 well plate, grown, and transferred into 24 well tissue culture plates (Costar Plastics) for maintenance. Culture supernatants were harvested for use in the screening assays for anti-*T. pallidum* reactivity and determination of monoclonal isotype.

E. Characterization of Monoclonal Antibody

RIA Screening Assays for Hybridomas Secreting Monoclonal Antibodies Against *T. pallidum*

To each well of a Cooke 96 well microtiter plate (Dynatech Laboratories, Alexandria, Va.) was added 10 μl of a suspension or sonicate of *T. pallidum* or *T. phagedenis* biotype Reiter containing the equivalent of $1\times10^8$ cells per ml in PBS or the rabbit testicular extract described earlier. Following incubation at 4° C. overnight to dryness, the wells were washed 3 times each with 0.2 ml portions of PBS containing 0.02% sodium azide to remove non-adhering antigen. Due to the strong affinity of treponemal and rabbit testicular tissue antigens for polyvinyl-chloride and other plastics, it was unnecessary to employ fixatives to promote binding of these antigens to the microtiter plate wells. If desired, however, 20 μl of 10% ethanol in each well followed by evaporation to dryness at 37° C. can be utilized for fixation. Wells were then precoated with 0.2 ml of PBS+1% (wt/vol) bovine serum albumin at 4° C. overnight, and washed 3 times with 0.2 ml of PBS+a- zide. Plates were used the same day or one day following preparation.

For the RIA test, 0.05 ml of a 4 day old hybridoma clone supernatant was added to each well containing a respective antigen preparation. After 3 hr at 23° C., the wells were washed 3 times with 0.2 ml PBS+azide, followed by the addition of $2.6 \times 10^5$ CPM of a mixture of affinity purified $^{125}$I-labeled rabbit anti-mouse IgG (specific activity of $2.0 \times 10^6$ CPM per $\mu$g) and IgM (specific activity of $3.7 \times 10^6$ CPM per $\mu$g) in 0.1 ml of PBS+azide+2% (vol/vol) horse serum per well. Binding of this probe was carried out overnight at 4° C. Wells were then washed extensively with PBS and tap water. Following drying of the plates and cutting of the individual wells, counting of the wells was performed in a Nuclear Chicago model 1185 gamma counter for 0.4 minute.

Antisera used as positive controls in the RIA included (1) mouse anti-*T. pallidum* serum collected from mice used as a source of splenic lymphocytes in cell fusions, and (2) mouse anti-rabbit testicular extract serum produced by immunizing BALB/c mice with rabbit testicular extract preparations. The mouse anti-rabbit testicular extract serum was generated by immunizing mice intraperitoneally on day 1 (0.25 ml testicular extract+0.25 ml complete Freund's adjuvant) and 0.3 ml of extract on days 30 and 51, followed by collection of the serum on day 72.

A total of 39 hybridoma cell lines were identified by RIA as secretors of monoclonal antibodies that reacted with *T. pallidum* antigens. Reactivity in the RIA was considered positive if $^{125}$I counts per 0.4 min were above 600 (background counts generally were in the order of 200-300). On this basis, the monoclonal antibodies arising from anti-*T. pallidum* hybridomas could be grouped into 3 major categories. One group of monoclonal antibodies was directed specifically against *T. pallidum* antigens; among these were monoclonal antibodies also capable of immobilizing virulent *T. pallidum* organisms in the *Treponema Pallidum Immobilization* test. Another group of monoclonal antibodies reacted with both *T. pallidum* and *T. phagedenis* biotype Reiter antigens and therefore was apparently directed against treponemal group antigens. A third group of monoclonal antibodies was capable of binding both treponemal and rabbit host testicular tissue antigens and thus was highly cross reactive with all antigens tested in the RIA.

Table 1 presents an example of the RIA protocol used to screen anti-*T. pallidum* hybrids. The data shown are from one of several typical RIA tests performed, and represent results characteristic of the majority of clones producing monoclonal antibodies specifically against *T. pallidum*. Monoclonal antibodies from such clones as those described in Table 1 did not react well with intact treponemes. However, they appeared to bind preferentially to sonicated antigens of *T. pallidum*, suggesting that they may be directed against either intracellular or "masked" antigens. Their specificity for *T. pallidum* determinants was indicated by their failure to cross react with *T. phagedenis* biotype Reiter antigen preparations and with rabbit testicular tissue antigens. These monoclonal antibodies were of mouse classes IgG and IgM, and were not reactive against *T. pallidum* in the TPI test. The polyclonal antisera preparations (mouse anti-*T. pallidum* and mouse anti-rabbit testicular tissue) used as positive controls in the RIA were strongly positive against all antigens tested. This was expected because the mouse anti-*T. pallidum* antibodies were derived from mice sensitized with *T. pallidum* suspensions containing both treponemal group antigens (that cross react with antigens of *T. phagedenis* biotype Reiter) as well as contaminating rabbit host antigens. Similarly, mouse anti-rabbit testicular antibodies also reacted with treponmal antigens due to the presence of shared antigens common to both rabbit host tissues and treponemes.

Monoclonal Antibody Isotype Assays

Mouse antibody isotypes were identified by solid phase RIA. Cooke microtiter plates were coated with goat anti-mouse immunoglobulin. Culture supernatants were then added and incubated for 3 hr at 37° C. Iodinated, affinity purified rabbit anti-mouse heavy chain specific reagents were added to identify the isotype of antibody bound to the plate.

TABLE 1

Radioimmunoassay ($^{125}$I counts/0.4 min) on five representative hybridoma cell lines producing monoclonal antibodies against *T. pallidum*

| | ANTIGENS | | | | | | |
|---|---|---|---|---|---|---|---|
| Clone | *T. pal*[1] | *T. pal*-aged[2] | *T. pal*-son[3] | Reiter[4] | Reiter-son[5] | Rabbit[6] | Antibody Isotype |
| 9B12 | 175 | 429 | 2,594 | 173 | 200 | 118 | IgG1 |
| 6F6 | 280 | 243 | 2,455 | 206 | 219 | 233 | IgM |
| 13D4 | 187 | 274 | 2,220 | 207 | 195 | 200 | IgG1 |
| 12D10 | 270 | 215 | 2,013 | 195 | 138 | 153 | IgG2a |
| 7E3 | 226 | 189 | 1,742 | 207 | 192 | 195 | IgG3 |
| Control Antisera: | | | | | | | |
| PBS | 229 | 220 | 298 | 252 | 175 | 214 | |
| DMEM Medium | 201 | 194 | 167 | 189 | 225 | 183 | |
| Mouse anti-*T. pal*[7]. | 20,049 | 20,691 | 21,274 | 18,433 | 12,399 | 11,424 | |
| Mouse anti-rabbit[8] | 18,314 | 17,973 | 19,872 | 15,826 | 13,646 | 18,799 | |

[1] Intact freshly isolated *T. pallidum*
[2] Intact, "aged" *T. pallidum*
[3] Sonicate of *T. pallidum*
[4] Intact *T. phagedenis* biotype Rieter
[5] Sonicate of *T. phagedenis* biotype Rieter
[6] Rabbit testicular extract
[7] 1:10 dilutions of mouse anti-*T. pallidum* serum from sensitized mice
[8] 1:10 dilution of mouse anti-rabbit testicular tissue extract serum.

Four hybridoma cell lines secreting antibodies specifically against *T. pallidum* were also isolated that appeared to produce monoclonal antibodies with greater affinity for possible surface determinants of *T. pallidum*

(see Table 2). Monoclonal antibodies from these clones possessed relatively high reactivity with both intact "aged" treponemes and sonicates of *T. pallidum,* but not with freshly isolated treponemes, with one possible exception, clone 7D7. Little or no cross reactivity with other treponemal or rabbit antigens was observed for these monoclonal antibodies. Despite their apparent increased specificity for possible surface components of *T. pallidum,* these monoclonal antibodies were also nonreactive in the TPI test.

Table 3 shows RIA data demonstrating anti-*T. pallidum* hybridoma cell lines producing monoclonal antibodies capable of reacting against *T. pallidum* in the TPI test. These clones secreted antibodies of the mouse isotypes which can fix complement. The antibodies did not react very well, however, with either freshly isolated intact or "aged" intact treponemes. This observation was surprising in view of the reactive TPI test data.

Because of the multitude of antigenic similarities known to exist between members of the genus Treponema it was not unexpected to generate hybridoma cell lines producing monoclonal antibodies that cross reacted with both *T. pallidum* and *T. phagedenis* biotype Reiter antigenic determinants. However, only 3 of 39 anti-*T. pallidum* hybridomas isolated possessed this characteristic (Table 4).

A class of hybridoma cell lines was also isolated that produced monoclonal antibodies found to cross react with all treponemal and rabbit testicular antigens employed in the RIA (Table 5). Because of the limiting dilution procedure employed and the fact that only one antibody isotype was observed for each cell line (except one clone 12H4), it is unlikely that these hybridoma cell lines represent more than one hybridoma clone growing together in culture. It may be of interest to note that all of these highly cross reactive antibodies were of the IgM class of antibody.

TABLE 2

Radioimmunoassay Results on anti-*T. pallidum* hybridomas producing monoclonal antibodies against "aged", intact treponemes.

| Clone | T. pal | T. pal-aged | T. pal-son | Reiter | Reiter-son | Rabbit | Antibody Isotype |
|---|---|---|---|---|---|---|---|
| 11E3 | − | + | + | − | − | − | IgG2a |
| 8G2 | − | + | + | − | − | − | IgG1 |
| 5C9 | − | + | + | − | − | − | IgM |
| 7D7 | + | + | + | − | − | − | IgM |

[1]Abbreviations and controls as in Table 1.

TABLE 3

Radioimmunoassay Results on anti-*T. pallidum* hybridomas secreting monoclonal antibodies reactive in the TPI test.

| Clone | T. pal | T. pal-aged | T. pal-son | Reiter | Reiter-son | Rabbit | Antibody Isotype |
|---|---|---|---|---|---|---|---|
| 3G5 | + | − | + | − | − | − | IgM |
| 13C6 | − | +, − | + | − | − | − | IgG2a |
| 5A7 | − | − | + | − | − | − | IgM |
| 13G10 | − | − | + | − | − | − | IgG2a |
| 4H7 | − | − | + | − | − | − | IgG2b |
| 13C8 | − | − | + | − | − | − | IgG2b |

[1]Abbreviations and controls as in Table 1.

TABLE 4

Rabioimmunoassay (Results) on anti-*T. pallidum* hybridomas secreting monoclonal antibodies that cross react with *T. phagedenis* biotype Reiter.

| Clone | T. pal | T. pal-aged | T. pal-son | Reiter | Reiter-son | Rabbit | Antibody Isotype |
|---|---|---|---|---|---|---|---|
| 13A7 | − | − | + | + | + | − | IgM |
| 1B11 | − | − | + | + | − | − | IgM |
| 12G11 | − | − | + | + | + | − | IgG2b |

[1]Abbreviations and controls as in Table 1.

TABLE 5

Rabioimmunoassay Results on hybridomas secreting monoclonal antibodies that bind *T. pallidum, T. phagedenis* biotype Reiter, and rabbit testicular antigens.

| Clone | T. pal | T. pal-aged | T. pal-son | Reiter | Reiter-son | Rabbit | Antibody Isotype |
|---|---|---|---|---|---|---|---|
| 1C11 | + | + | + | + | + | + | IgM |
| 12F4 | + | + | + | + | + | + | IgM |
| 1870-5A5 | + | + | + | + | + | + | IgM |
| 6A9 | + | + | + | + | + | + | IgM |

TABLE 5-continued

Rabioimmunoassay Results on hybridomas secreting monoclonal antibodies that bind *T. pallidum, T. phagedenis* biotype Reiter, and rabbit testicular antigens.

| Clone | ANTIGENS[1] | | | | | | Antibody Isotype |
|---|---|---|---|---|---|---|---|
| | T. pal | T. pal-aged | T. pal-son | Reiter | Reiter-son | Rabbit | |
| 12E3 | − | + | + | +, − | + | + | IgM |

[1]Abbreviations and controls as in Table 1.

Monoclonal Antibodies in the *Treponema pallidum* Immobilization (TPI) Test.

Mouse anti-*T. pallidum* serum, mouse anti-rabbit testicular extract serum, and monoclonal antibodies secreted by anti-*T. pallidum* hybridomas were tested for their ability to immobilize virulent *T. pallidum* (Nichols) in the *Treponema pallidum* immobilization (TPI) test. The TPI assay was carried out, with minor modifications, as described in the Manual of Tests for Syphilis (Center for Disease Control, 1964, Dept. of Health, Education and Welfare, Public Health Service, N.C.D.C., Atlanta, Ga.). Penicillinase was incorporated in the test procedure due to the presence of penicillin in the hybridoma clone supernatants. Because *T. pallidum* was not sensitive to streptomycin at the concentrations employed in the medium, removal of streptomycin from the hybridoma clone supernatants was unnecessary.

The following hybridomas exhibited both *T. pallidum* specificity and TPI-reactivity:

| CLONE | ANTIBODY ISOTYPE |
|---|---|
| 3G5 | IgM |
| 4H7 | IgG2b |
| 5A7 | IgM |
| 13C6 | IgG2a |
| 13C8 | IgG2b |
| 13G10 | IgG2a |

Microhemagglutination (MHA-TP) Test for *Treponema Pallidum* Antibodies

The MHA-TP test (Sera-Tek Treponemal Antibody Test, Ames Division, Miles Laboratories, Inc.) was performed as described by the manufacturers. Briefly, 3 μl of each fourday old hybridoma clone supernatant (DMEM medium) containing anti-*T. pallidum* monoclonal antibodies were mixed with 57 μl of absorbing diluent (1:20 dilution) and allowed to incubate at room temperature for 30 minutes. For each monoclonal antibody preparation, 25 μl aliquots of the absorbed monoclonal antibody mixture were then added in duplicate wells of a 96 well microtiter plate. For each clone sample, 75 μl of sensitized sheep erythrocytes were added to one set of wells and 75 μl of unsensitized sheep erythrocytes were added to the other duplicate wells as a negative control.

Reactive clones were 8G2 and 11E3; all other hybridoma clone supernatants tested were non-reactive.

It appeared that a greater degree of anti-*T. pallidum* specificity was exhibited by IgG secreting clones as opposed to those clones secreting IgM. Table 6 summarizes the isotypes of all murine anti-*T. pallidum* monoclonal antibodies, their specificities, and their frequency of isolation in this study. A majority (24 of 31 clones) of the hybridomas isolated that reacted only against *T. pallidum* antigens were of IgG subclasses, compared to 7 IgM clones with similar properties. Of 8 total clones that cross reacted with either *T. phagedenis* biotype Reiter or rabbit testicular antigens, 7 of these were IgM producers.

TABLE 6

Summary of monoclonal antibody characteristics from 39 anti-*T. pallidum* hybridomas.
Antibody Specificities[1]

| Mouse Antibody Isotype | T. pal | T. pal + Reiter | T. pal + Reiter + Rabbit | Total |
|---|---|---|---|---|
| IgM | 7[2] | 2 | 5 | 14 |
| IgG3 | 2 | 0 | 0 | 2 |
| IgG1 | 11[4] | 0 | 0 | 11 |
| IgG2b | 3[2] | 1 | 0 | 4 |
| IgG2a | 7[2],[4] | 0 | 0 | 7 |
| IgG1,IgG2b[3] | 1 | 0 | 0 | 1 |
| Total | 31 | 3 | 5 | 39

Moreover, the monoclonal antibodies potentially provide new affinity purification reagents that can be used to isolate and purify *T. pallidum* cells from rabbit tissue, which is currently performed by very expensive and inefficient methods. Through the use of monoclonal antibody affinity column chromatography, affinity purified *T. pallidum* cells can be prepared and employed as diagnostic antigen in currently existing serodiagnostic tests for syphilis. Such affinity purified treponemal cells may also increase the sensitivity of the pre-existing tests since this material will be much "cleaner" than conventionally prepared *T. pallidum* cells (i.e., free of contaminating rabbit tissue debris). Also, in lieu of whole *T. pallidum* cells as an antigen in serodiagnostic tests, the monoclonal antibodies may possess the ability to affinity purify newly-defined antigen components of *T. pallidum* cells that can be used in place of whole treponemal cells as test antigen. Consequently, the monoclonal antibodies have the ultimate potential of both identifying new antigenic components of the organism as well as the ability to purify them out from fractionated *T. pallidum* cells.

Ultimately, the affinity purified *T. pallidum* antigen components may be used to develop a vaccine for syphilis. Although only targeted segments of the U.S. population would most likely be candidates for such a vaccine (i.e., gay populations, migrant workers, inner city dwellers, etc.), there are other important treponemal diseases against which such a vaccine might be effective. Briefly, the treponemes that cause yaws, pinta, and bejel are treponemes that are morphologically and serologically indistinguishable from *T. pallidum.* Because of the immunological similarities of the yaws, pinta, and bejel organisms to *T. pallidum,* a vaccine developed against syphilis may be just as effective against these endemic treponemal diseases. Thus, the ability to prepare affinity purified antigens (immunogens) of *T. pallidum* that are immunogenic may have a very broad application to treponemal disease vaccines in general.

The foregoing description of the invention has been directed to particular embodiments for purposes of explanation and illustration. It will be apparent, however, to those skilled in the art that many modifications and changes in the processes of preparing and implementing the described embodiments may be made without departing from the essence of the invention. It is applicants' intention in the following claims to cover all equivalent modifications and variations as fall within the scope of the invention.

What is claimed is:

1. A composition of matter consisting essentially of a continuous murine hybrid cell line that produces monoclonal antibody against an antigenic determinant of *Treponema pallidum,* which cell line is formed as a fusion between a murine myeloma cell and a differentiated murine lymphoid cell immunized with *Treponema pallidum* antigen.

2. The composition of claim 1 wherein the continuous hybrid cell line is together with a culture medium suitable for supporting growth of the cell line.

3. The composition of claim 1 wherein the myeloma cell is a hybridoma cell or plasmacytoma cell.

4. The composition of claim 1 wherein the differentiated lymphoid cell is an immune spleen cell or lymph node cell.

5. The composition of claim 1 wherein the continuous hybrid cell line is a celled hybrid of a BALB/c mouse immune spleen cell immunized against *Treponema pallidum* antigens, fused to a SP2/0 hyridoma cell.

6. The composition of claim 1 wherein the hybrid cell line consists essentially of hybridoma clone indentified as ATCC deposit HB8133 or HB8134.

7. A composition of matter consisting essentially of monoclonal antibodies directed against an antigenic determinant of *Treponema pallidum,* said antibodies produced from a continuous murine hybrid cell line formed by fusing a murine myeloma cell with a differentiated murine lumphoid cell immunized against *Treponema pallidum* antigens.

8. The composition of claim 7 wherein the monoclonal antibodies are capable of fixing complement and immobilizing virulent *Treponema pallidum* organisms.

9. The composition of claim 7 wherein the monoclonal antibodies are produced by the hybrid cell lines identified as ATCC deposit HB8133 or HB8134.

* * * * *